United States Patent [19]

Weddendorf

[11] Patent Number: 5,267,950
[45] Date of Patent: Dec. 7, 1993

[54] AUTOMATIC LOCKING ORTHOTIC KNEE DEVICE

[75] Inventor: Bruce C. Weddendorf, Huntsville, Ala.

[73] Assignee: The United States of America as represented by the Administrator of the National Aeronautics and Space Administration, Washington, D.C.

[21] Appl. No.: 813,629

[22] Filed: Dec. 26, 1991

[51] Int. Cl.$^5$ .............................................. A61F 5/00
[52] U.S. Cl. ...................................... 602/26; 602/16; 623/43; 623/44
[58] Field of Search ................... 602/12, 5, 16, 26; 128/80 C, 882; 623/43, 44, 45; 403/72, 79, DIG. 3, 94, 97, 2; 188/15, 24.18, 371, 250 R

[56] References Cited

U.S. PATENT DOCUMENTS

| | | | |
|---|---|---|---|
| 2,594,227 | 5/1951 | Smith | 602/26 X |
| 3,826,251 | 7/1974 | Ross | 602/16 |
| 4,252,111 | 2/1981 | Chao et al. | 602/16 |
| 4,632,096 | 12/1986 | Harris | 602/16 |

*Primary Examiner*—Robert Bahr
*Assistant Examiner*—Beverly A. Meindl
*Attorney, Agent, or Firm*—Robert L. Broad, Jr.; Guy M. Miller; John R. Manning

[57] ABSTRACT

An articulated tang in clevis joint for incorporation in newly manufactured conventional strap-on orthotic knee devices or for replacing such joints in conventional strap-on orthotic knee devices. The instant tang in clevis joint allows the user the freedom to extend and bend the knee normally when no load (weight) is applied to the knee and to automatically lock the knee when the user transfers weight (load) to the knee, thus preventing a damaged knee from bending uncontrollably when weight (load) is applied to the knee.

The tang in clevis joint of the present invention includes first and second clevis plates, a tang assembly and a spacer plate sandwiched and secured between the clevis plates. Each clevis plate includes a bevelled serrated upper section. A bevelled shoe is secured to the tang in close proximity to the bevelled serrated upper section of the clevis plates. A coiled spring mounted within an oblong bore of the tang normally urges (when no weight is applied to the joint) the shoes secured to the tang out of engagement with the serrated upper section of each clevis plate to allow rotation of the tang relative to the clevis plate. When weight (load) is applied to the joint, the load compresses the coiled spring, the serrations on each clevis plate dig into the bevelled shoes secured to the tang to prevent relative movement between the tang and clevis plates. A shoulder is provided on each of the tang and the spacer plate to prevent overextension of the joint.

19 Claims, 3 Drawing Sheets

AUTOMATIC LOCKING ORTHOTIC KNEE DEVICE

ORIGIN OF THE INVENTION

The invention described herein was made by an employee of the United States Government and may be manufactured and used by or for the Government for governmental purposes without the payment of any royalties thereon or therefor.

FIELD OF THE INVENTION

The present invention relates generally to joints for strap-on orthotic knee devices. More particularly, this invention relates to joints which allow the user freedom to extend and bend the knee normally when load is not applied to the joint, to automatically lock the joints when load is applied thereto, and to automatically unlock the joints when load is removed therefrom.

BACKGROUND OF THE INVENTION

The prior art abounds with strap-on orthotic knee devices to be worn by persons recuperating from surgery or injuries to the knees. Most of the prior art devices include a strap-on thigh engaging section and a strap-on leg engaging section connected by a pair of tang in clevis joints which permit the user the freedom to extend and bend the knee over a full range. One currently available strap-on orthotic knee device incorporates tang in clevis joints with automatically engaging locking devices which snap in at full extension of the knee joint and requires the manual disengagement of the locking device by means of a finger loop to allow bending of the joint.

The prior art strap-on orthotic knee device with the automatically engaging locking device has two major drawbacks or disadvantages. The first drawback or disadvantage is due to the fact that the locking, while automatic, can occur only when the user has achieved full extension of the knee. This creates a safety hazard and causes accidents in that the user may not be able to fully extend the knee before loading (placing weight on) the leg, which could cause the knee to fold uncontrollably, and permit the user to fall. The second drawback or disadvantage relates to the manual operation required to disengage or unlock the joint, which operation is cumbersome in that the user must have a free hand to devote to the control loop and could discourage the user from the therapeutic bending of the knee.

The present invention overcomes the disadvantages, drawbacks or deficiencies of the prior art devices in that it provides a rapid, automatic, locking and unlocking of the joint according to the load being carried by the joint. The joint of the present invention automatically locks when weight is applied thereto, even when the knee is slightly bent, thus allowing the joint to remain free to rotate when unloaded, to permit more freedom of motion and mobility to the user. The rapid, automatic, loading and unloading of the joint prevents accidents and encourages the user to exercise the knee to rehabilitate same.

Accordingly, it is an object of the present invention to provide a new and improved tang in clevis joint for strap-on orthotic knee devices which incorporates locking and unlocking structure which is rapid and automatic in operation and prevents the unwanted folding of the joint.

It is a further object of the present invention to provide a rapid and automatic locking and unlocking tang in clevis joint for strap-on orthotic knee devices which prevents accidents, encourage exercise by the user, and aids in the rehabilitation of the injured knee.

It is still a further object of the present invention to provide a tang in clevis joint for strap-on orthotic knee devices which automatically locks and unlocks the knee to allow the free rotation of the knee and the locking of the knee as desired.

Other aspects, objects and advantages of this invention will become apparent to those skilled in the art to which this invention pertains from a study of the preferred embodiment as set forth in the specifications, drawings and the appended claims.

SUMMARY OF THE INVENTION

In accordance with the present invention, a tang in clevis joint is provided which ca be incorporated in newly manufactured conventional strap-on orthotic knee devices or for replacing such tang in clevis joints in the conventional strap-on orthotic knee devices. Two such tang in clevis joints are normally incorporated in conventional strap-on orthotic knee devices, one on each side of the knee with each being connected to a thigh engaging section and a leg engaging section.

The tang in clevis joint of the present invention allows the user the freedom to extend and bend the knee normally when n load (weight) is applied to the knee and to automatically lock the knee when the user transfers weight (load) to the knee. This locking feature prevents the user's damaged knee from bending uncontrollably when weight is applied to the knee and is effective over a range of motion from fully extended to the order of forty-five degrees (45°) of bend in the joint. The locking and unlocking of the joint is silent and allows the user greater mobility and safety.

The tang in clevis joint of the present invention includes first and second clevis plates, a tang assembly and a spacer plate sandwiched and secured between the clevis plates. Each clevis plate includes a bevelled serrated upper section. A bevelled shoe is secured to the tang in close proximity to the bevelled serrated upper section of the clevis plates. A coiled spring mounted within an oblong bore of the tang normally urges (when no weight is applied to the joint) the shoes secured to the tang out of engagement with the serrated upper section of each clevis plate to allow rotation of the tang relative to the clevis plate. When weight (load) is applied to the joint, the load compresses the coiled spring, the serrations on each clevis plate dig into the bevelled shoes secured to the tang to prevent relative movement between the tang and clevis plates. A shoulder is provided on each of the tang and the spacer plate to prevent overextension of the joint.

DESCRIPTION OF THE PREFERRED EMBODIMENT

Figure 1:
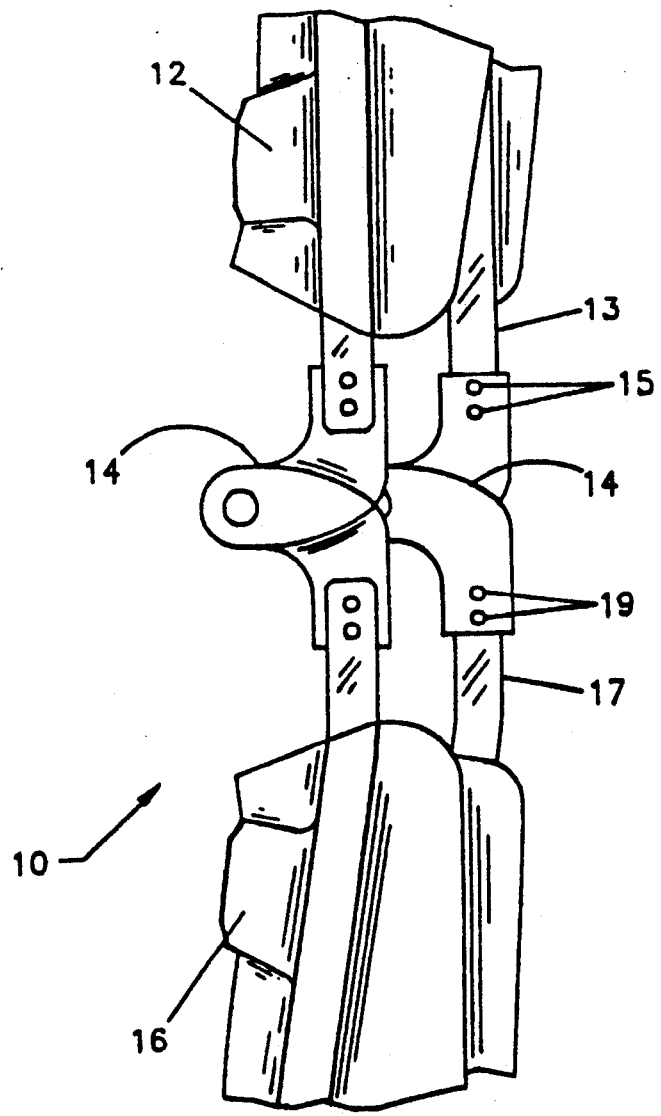
FIG. 1 is a perspective, partially broken-away, view of the prior art orthotic knee brace and joints.

Referring to the drawings, FIG. 1 is illustrative of a prior art orthotic knee brace 10 comprising a thigh engagement section 12, tang in clevis joints 14, and a leg engagement section 16. The upper portion of each tang in clevis joint 14 is connected to the lower end of a first pair of struts or arms 13 by any suitable means such as two screws or rivets 15 extending through bores (not shown) in struts or arms 13 with the upper end of each strut or arm 13 being connected to the lower portion of the thigh engagement section 12 by any suitable means (not shown) such as adhesives, screws or rivets. The lower portion of each tang in clevis joint 14 is connected to a second pair of struts or arms 17 by any suitable means such as two screws or rivets 19 extending through bores (not shown) in struts or arms 17 with the lower end of each strut or arm 17 being connected to the upper portion of leg engagement section 16 by any suitable means (not shown) such as adhesives, screws or rivets. The tang in clevis joint 14 in one prior art orthotic knee brace 10 incorporates an automatically engaged locking device (details not shown) which snaps in at full extension of the leg and requires the manual disengagement of the locking device to allow bending of the knee.

Figure 2:
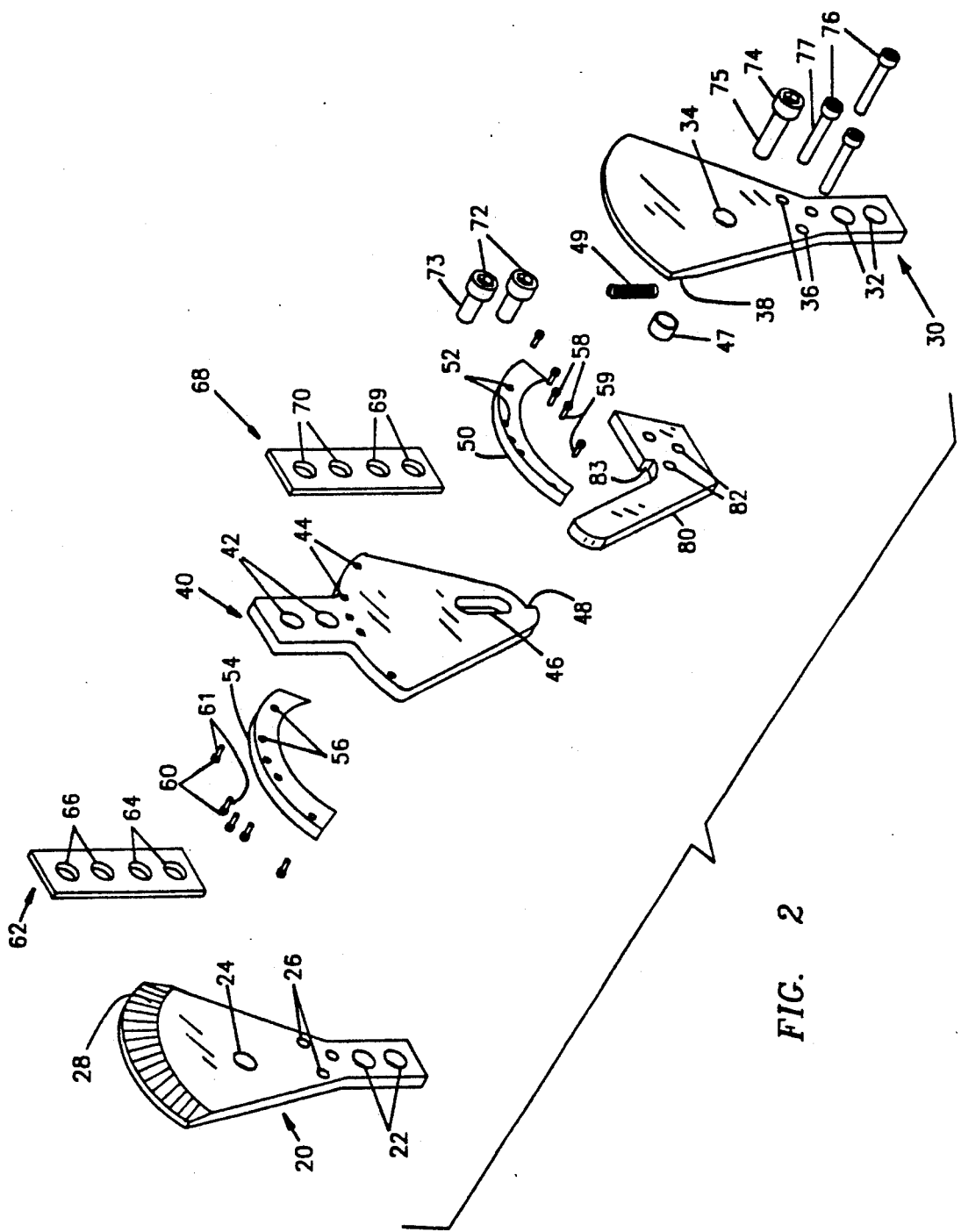
FIG. 2 is an exploded, perspective, view of the automatic orthotic knee joint of the present invention.
Figure 4:
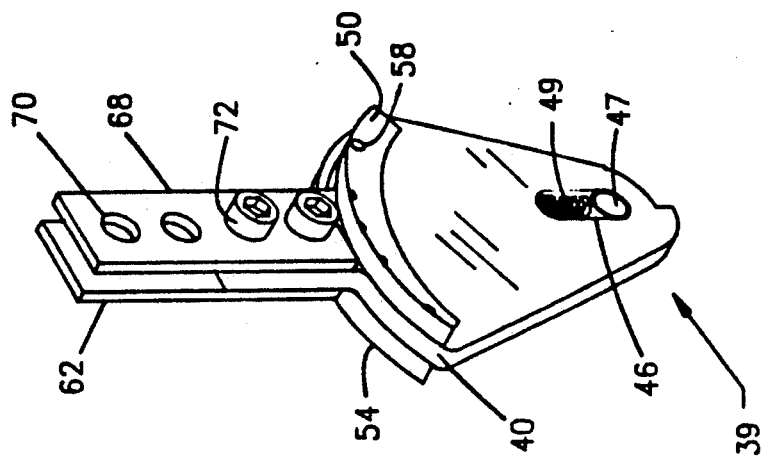
FIG. 4 is a perspective view of a tang assembly for the orthotic knee joint of the present invention.
Figure 3:
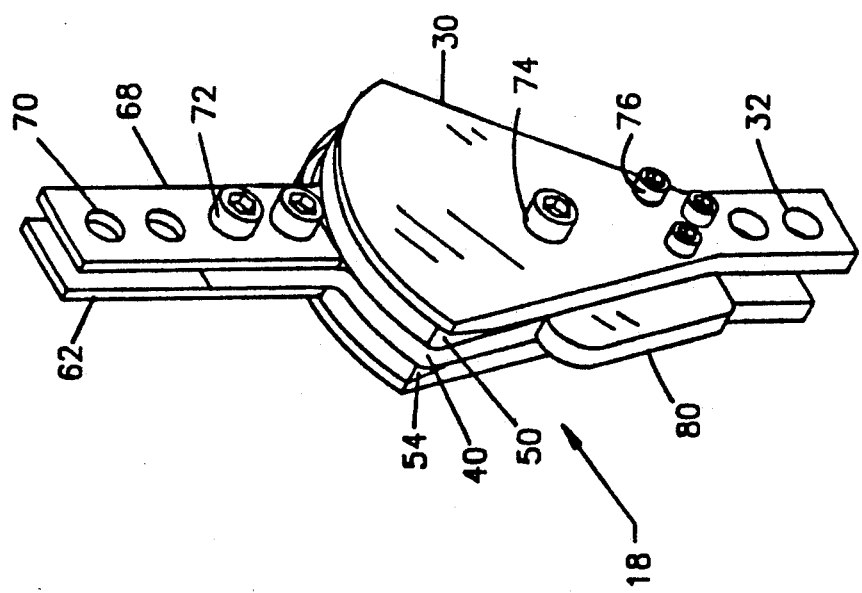
FIG. 3 is a perspective view of an assembled orthotic knee joint of the present invention.

The automatically locking tang in clevis knee joint 18 of the present invention is illustrated in its nonassembled or exploded condition in FIG. 2 and in its assembled condition in FIG. 3. Tang in clevis knee joint 18 comprises a first clevis plate 20, a second clevis plate 30, a tang assembly 39 (FIG. 4), and a spacer plate 80 secured together by bolts 74 and 76. Tang assembly 39 is secured together by bolts 72.

As best illustrated in FIG. 2, first clevis plate 20 includes two threaded bores 22, a threaded bore 24, three threaded bores 26, and a bevelled serrated, upper, surface 28. Second clevis plate 30 includes two unthreaded bores 32, an unthreaded bore 34, three unthreaded bores 36, and a beveled serrated, upper, surface 38. Tang assembly 39 includes a tang 40, two unthreaded bores 42, five threaded bores 44 extending through tang 40, an oblong slot 46, a bushing 47 and a coiled spring 49 for mounting within oblong slot 46, a shoulder 48, a first shoe 50 having five countersunk openings 52 therein, a second shoe 54 having five countersunk openings 56 therein, five screws 58 having threads 59 for mounting within countersunk bores 52 of first shoe 50 and engagement with threaded bores 44 in tang 40, five screws 60 having threads 61 for mounting within countersunk bores 56 in second shoe 54 and engagement with threaded bores 44 in tang 40, a first strap 62 having two threaded bores 64 and two threaded bores 66, a second strap 68 having two unthreaded bores 69 and two unthreaded bores 70, and a pair of allen head bolts 72 having threads 73 for insertion through unthreaded bores 69 in second strap 68, unthreaded bores 42 in tang 40, and threaded bores 64 in first strap 62 with threads 73 positively engaging the threads in threaded bores 64 to secure together the entire tang assembly 39. Spacer 80 includes three unthreaded bores 82 and a shoulder 83. First clevis plate 20 and second clevis plate 30 are secured to the tang assembly 39 and spacer 80 by three allen head bolts 76 having threads 77 which pass through the unthreaded bores 36 in second clevis plate 30, the unthreaded bores 82 in spacer 80 and the threaded bores 26 in first clevis plate 20 with the threads 77 of the allen head bolts 76 being in positive threaded engagement with threaded bores 26 in first clevis plate 20, and by allen head bolt 74 having threads 75 which pass through unthreaded opening 34 in second clevis plate 30, the opening in bushing 47 of tang assembly 39 and the threaded bore 24 in first clevis plate 20 with the threads 75 of bolt 74 in positive engagement with the threads of bore 24 in first clevis plate 20.

Each tang in clevis joint 18 of the present invention is assembled or connected to the lower end of one of the pair of struts or arms 13 (FIG. 1) extending from and connected to the thigh engagement section 12 of an orthotic knee brace 10 such as that illustrated in FIG. 1 by inserting the lower end of the appropriate strut or arm 13 into the space separating the upper end of straps 62 and 68 and inserting a threaded screw 15 through each unthreaded bore 70 in strap 68, each unthreaded bore (not shown) in the lower end of strut or arm 13, and into threaded engagement with a threaded bore 66 in strap 62. Each tang in clevis joint 18 of the present invention is assembled or connected to the upper end of one of the pair of struts or arms 17 (FIG. 1) extending from and connected to the leg engagement section 16 of an orthotic knee brace 10 such as that illustrated in FIG. 1 by inserting the upper end of the appropriate strut or arm 17 into the space separating the lower portion of clevis plates 20 and 30 and inserting a threaded screw 19 through each unthreaded bore 32 in clevis plate 30, each unthreaded bore (not shown) in the upper end of strut or arm 17, and into threaded engagement with a threaded bore 22 in clevis plate 20.

Clevis plates 20 and 30 are preferably made of a hard steel such as Crescent steel; main plate 40 of tang assembly 39 is preferably made of aluminum; and shoes 50 and 54 are preferably made of a soft brass; however, these elements could be made of other materials. The serrations 28 and 38 in first clevis plate 20 and second clevis plate 30, respectively, are preferably radially cut; however, the cuts could be other than radially. The bevelled surfaces of shoes 50 and 54 might also incorporate serrations or have other conventional material applied thereto if additional frictional engagement were deemed necessary or desirable between shoes 50 and 54 and the serrations 38 and 28, respectively, of clevis plates 20 and 30.

In operation, thigh engaging section 12 and leg engaging section 16 are strapped or fastened to the thigh and leg, respectively, by conventional straps (not shown) attached thereto. When weight or pressure is applied to a joint 18, spring 49 is compressed to allow the serrations 28 and 38 on clevis plates 20 and 30, respectively, to bite into the bevelled surfaces of shoes 50 and 54, respectively, and prevent relative, rotational movement between the clevis plates 20 and 30 and the main plate 40. When weight or pressure is relieved from the joint 18, spring 49 acting on the wall of oblong slot 46 forces the main plate 40 and its shoes 50 and 54 in an upward direction away from the serrations 28 and 38 to allow relative, rotational, movement between the clevis plates 20 and 30 and the main plate 40. When weight or pressure is released from joint 18, the shoulder 48 on main plate 40 and shoulder 83 on spacer 80 serve as a stop to prevent an overextension of the knee.

While the above description constitutes a preferred embodiment of the present invention, it will be appreciated that the invention is susceptible to modification, variation and change without departing from the proper scope and fair meaning of the accompanying claims.

I claim:

1. An automatically locking and unlocking joint for use in a strap-on orthotic knee device including a thigh engaging section, a leg engaging section, and a pair of struts connected to and extending from each of said thigh engaging section and said leg engaging section, said joint comprising:

first support means having an upper frictional surface and a lower depending portion disposed for attachment to said pair of struts connected to and extending from said leg engaging section;

second support means having an upper extending portion disposed for attachment to said pair of struts connected to and extending from said thigh engaging section, a lower portion having downwardly extending stop means and a frictional surface disposed for releasable engagement with said upper frictional surface of said first support means;

means for pivotally mounting said first and second support means together;

third support means mounted on said second support means, said third support means having an upwardly extending stop means for cooperating with said stop means of said second support means for preventing an overextension of said joint; and biasing means mounted in said second support means and acting on said pivot mounting means and said second support means for normally urging said frictional surface of said second support means out of engagement with said frictional surface of said first support means, said biasing means being responsive to the application of force on said second support means to cause said frictional surface of said second support means to engage said frictional surface of said first support means to prevent pivotal movement between said first and second support means.

2. The automatically locking and unlocking joint of claim 1 wherein said frictional surface of said first support means includes a plurality of serrations.

3. The automatically locking and unlocking joint of claim 2 wherein said plurality of serrations are disposed radially and arcuately on a bevelled upper surface of said first support means.

4. The automatically locking and unlocking joint of claim 3 wherein said frictional surface of said second support means include an arcuate, bevelled, shoe.

5. The automatically locking and unlocking joint of claim 4 wherein said first support means is made of a hardened steel and said shoe is made of a soft brass.

6. The automatically locking and unlocking joint for use in a strap-on orthotic knee device including a thigh engaging section, a leg engaging section, and a pair of struts connected to and extended from each of said thigh engaging section and said leg engaging section, said tank in clevis joint comprising:

a first clevis plate having an upper frictional surface;

a second clevis plate having an upper frictional surface;

a tang assembly comprising a main plate having two sides and a shoe mounted on each said side of said main plate;

means for pivotally securing said first and second clevis plates to said main plate of said tang assembly;

means for securing said tang assembly to the struts connected to and extending from the thigh engaging section of the strap-on orthotic knee device;

means for securing said first and second clevis plates to the struts connected to and extending from the leg engaging section of said strap-on orthotic knee device; and biasing means for acting on the main plate of said tang assembly for normally urging said shoes mounted on said tang plate out of engagement with said frictional surfaces of said first and second clevis plates, but responsive to a load being placed upon said tang assembly for causing said frictional surfaces of said first and second clevis plates to engage said shoes on said main plate to prevent pivotal movement between said clevis plates and said main plate.

7. The automatically locking and unlocking joint of claim 6 wherein said means for securing said first and second clevis plates to said main plate includes an unthreaded bore in said second clevis plate, threaded bore in said first clevis plate, and a bolt having threads for engaging said threaded bore in said first clevis plate.

8. The automatically locking and unlocking joint of claim 7 wherein said means for securing said tank assembly to the struts connected to and extending from the thigh engaging section of the strap-on orthotic knee device includes a pair of straps secured to said tang assembly, one of said straps having at least one unthreaded bore therein with the other of said straps having at least one threaded bore therein.

9. The automatically locking and unlocking joint of claim 8 wherein said means for securing said first and second clevis plates to the struts connected to and extending from the leg engaging section of the strap-on orthotic knee device includes at least one unthreaded bore in said second clevis plate and at least one threaded bore in said first clevis plate.

10. The automatically locking and unlocking joint of claim 9 wherein said main plate of said tang assembly includes an oblong slot therein and said biasing means for normally urging said shoes mounted on said tang plate out of engagement with said fictional surfaces of said first and second clevis plates includes a spring mounted within said oblong slot.

11. The automatically locking and unlocking join of claim 6 wherein said frictional surfaces of said first and second clevis plates includes a plurality of serrations.

12. The automatically locking and unlocking joint of claim 11 wherein said first and second clevis plates are made of a hard steel and wherein said shoes are made of brass to enable said serrations on said clevis plates to dig into said shoes when weight is applied to said joint.

13. The automatically locking and unlocking joint of claim 12 including means for limiting pivotal movement of said tang assembly relative to said first and second clevis plates to prevent overextension of the joint.

14. The automatically locking and unlocking joint of claim 13 wherein said means for limiting pivotal movement of said tank assembly and said first and second clevis plates include a spacer plate having an upwardly extending stop means for engagement with a downwardly extending stop means on said main plate.

15. An automatically locking and unlocking tang in clevis joint for use in a strap-on orthotic knee device including a thigh engaging section, a leg engaging section, and a pair of struts connected to and extending from each of said thigh engaging section and said leg engaging section, said tang in clevis joint comprising:

a first clevis plate including a lower portion and an upper portion, said upper portion having an arcuate, bevelled, surface including a plurality of serrations thereon;

a second clevis plate including a lower portion and an upper portion, said upper portion having an arcuate, bevelled, surface including a plurality of serrations thereon;

a spacer plate between said first and second clevis plates;

a tang assembly comprising a main plate having an upper portion and two sides, and an arcuate, bevelled, shoe mounted on each said side of said main plate;

means for pivotally securing said first and second plates to said main plate of said tang assembly and said spacer plate;

means for securing said upper portion of said tank assembly to said struts connected to and extending from the thigh engaging section of the strap-on orthotic knee device;

means for securing said lower portion of said first and second clevis plates to the struts connected to and extending from the leg engaging section of the strap-on orthotic knee device; and means for acting on said main plate of said tang assembly for normally urging said arcuate, bevelled, shoes mounted on said tang plate out of engagement with said serrations on said arcuate, bevelled, surfaces of sad upper portions of said first and second clevis plate, but responsive to a load being placed upon said tang assembly for causing said frictional means on said first and second clevis plates to engage said shoes on said main plate to prevent pivotal movement between said clevis plates and said main plate.

16. The automatically locking and unlocking tang in clevis joint of claim 15 wherein said means for pivotally securing said first and second clevis plates to said main plate includes an unthreaded bore in said second clevis plate, a threaded bore in said first clevis plate, and a bolt having threads for engaging said threaded bore in said first clevis plate.

17. The automatically locking and unlocking tang in clevis joint of claim 16 wherein said means for normally urging said arcuate, bevelled, shoes mounted on said tang plate out of engagement with said serrations on said upper portions of said first and second clevis plates includes a spring mounted within an oblong slot in said tang plate.

18. The automatically locking and unlocking tang in clevis joint of claim 17 including means for limiting pivotal movement of said tang assembly relative to said spacer plate.

19. The automatically locking and unlocking tank in clevis join of claim 17 wherein said spacer plate has an upwardly extending stop means and wherein said main plate has downwardly extending stop means, which stop means of said main plate engages said stop means of said spacer plate to limit pivotal movement between said clevis and said tang assembly to prevent an overextension of the joint.

* * * * *